(12) United States Patent
Voit et al.

(10) Patent No.: US 9,931,771 B2
(45) Date of Patent: Apr. 3, 2018

(54) SOFTENING MATERIALS BASED ON THIOL-ENE COPOLYMERS

(71) Applicant: The Board of Regents of the University of Texas System, Austin, TX (US)

(72) Inventors: Walter Voit, Dallas, TX (US); Taylor Ware, Beavercreek, OH (US)

(73) Assignee: The Board of Regents of the University of Texas System, Austin, TX (US)

( * ) Notice: Subject to any disclaimer, the term of this patent is extended or adjusted under 35 U.S.C. 154(b) by 167 days.

(21) Appl. No.: 14/261,336

(22) Filed: Apr. 24, 2014

(65) Prior Publication Data

US 2014/0323647 A1    Oct. 30, 2014

Related U.S. Application Data

(60) Provisional application No. 61/815,607, filed on Apr. 24, 2013, provisional application No. 61/815,603, filed on Apr. 24, 2013.

(51) Int. Cl.

| | |
|---|---|
| *A61L 27/18* | (2006.01) |
| *B29C 45/00* | (2006.01) |
| *B23K 26/00* | (2014.01) |
| *B29C 67/00* | (2017.01) |
| *C08F 120/36* | (2006.01) |
| *C08K 3/04* | (2006.01) |
| *H04R 25/00* | (2006.01) |
| *B23K 26/402* | (2014.01) |
| *B33Y 10/00* | (2015.01) |
| *B33Y 30/00* | (2015.01) |
| *B29K 105/00* | (2006.01) |
| *B29K 105/12* | (2006.01) |
| *B29L 31/00* | (2006.01) |
| *B29C 33/38* | (2006.01) |
| *B29C 33/40* | (2006.01) |
| *B33Y 80/00* | (2015.01) |
| *B33Y 99/00* | (2015.01) |
| *B23K 103/00* | (2006.01) |

(52) U.S. Cl.
CPC .............. *B29C 45/00* (2013.01); *B23K 26/00* (2013.01); *B23K 26/0075* (2013.01); *B23K 26/402* (2013.01); *B29C 67/0066* (2013.01); *B29C 67/0085* (2013.01); *C08F 120/36* (2013.01); *C08K 3/04* (2013.01); *H04R 25/652* (2013.01); *A61F 2240/004* (2013.01); *B23K 2203/42* (2015.10); *B29C 33/3807* (2013.01); *B29C 33/40* (2013.01); *B29K 2105/0002* (2013.01); *B29K 2105/0005* (2013.01); *B29K 2105/0032* (2013.01); *B29K 2105/0044* (2013.01); *B29K 2105/0058* (2013.01); *B29K 2105/12* (2013.01); *B29L 2031/7532* (2013.01); *B33Y 10/00* (2014.12); *B33Y 30/00* (2014.12); *B33Y 80/00* (2014.12); *B33Y 99/00* (2014.12)

(58) Field of Classification Search
CPC ...................................................... A61L 27/18
See application file for complete search history.

(56) References Cited

U.S. PATENT DOCUMENTS

| | | | | |
|---|---|---|---|---|
| 4,052,283 | A * | 10/1977 | Dannels .................. | C08G 75/14 522/1 |
| 2009/0253805 | A1* | 10/2009 | Hoyle ................... | C07C 323/52 514/772.3 |
| 2010/0305309 | A1* | 12/2010 | Ho .................... | A61K 47/48853 530/402 |
| 2011/0144227 | A1* | 6/2011 | Bowman ................. | A61L 27/18 522/96 |
| 2012/0308532 | A1* | 12/2012 | Hult ........................ | A61L 27/26 424/93.7 |

* cited by examiner

*Primary Examiner* — Michael Pepitone (57) ABSTRACT

Embodiments of the invention are directed to softening amorphous polymeric materials based on a combination of thiol, acrylate, ene and epoxy monomers. These materials can soften to the modulus of tissue, have a sharp transition and are highly tunable. The materials have a glassy modulus of 1-7 GPa and exhibit a rubbery plateau in modulus that can range from 100 MPa down to as low as 0.03 MPa, which is at or below the modulus of tissue. They have potential uses as materials for near net shape processing such as casting, stereolithography, reaction injection molding, fused deposition molding and various other forms of 3D printing.

22 Claims, 5 Drawing Sheets

SOFTENING MATERIALS BASED ON THIOL-ENE COPOLYMERS

CROSS-REFERENCES TO RELATED APPLICATIONS

This application claims the benefit under 35 U.S.C. § 119(e) of U.S. Provisional Patent Application No. 61/815,603 filed Apr. 24, 2013, and U.S. Provisional Patent Application No. 61/815,607 filed Apr. 24, 2013, which are incorporated herein by reference in its entirety as if fully set forth herein.

FIELD OF THE INVENTION

The claimed invention is directed to softening amorphous polymeric materials based on a combination of thiol, acrylate, ene and epoxy monomers. These materials can soften to the modulus of tissue, have a sharp transition and are highly tunable. The materials have a glassy modulus of 1-3 GPa and exhibit a rubbery plateau in modulus that can range from 100 MPa down to as low as 0.03 MPa, which is at or below the modulus of tissue. They have potential uses as materials for near net shape processing such as casting, stereolithography, reaction injection molding, fused deposition molding and various other forms of 3D printing.

BACKGROUND OF THE INVENTION

Silicone polymers display an exceptionally wide range of chemistries and physical properties. These polymers can be low viscosity liquids, crosslinkable elastomers, or hard solids. Applications for silicone sealants are extremely broad. Markets include construction, automotive, assembly, maintenance, electrical/electronic, aerospace, and consumer products. Silicone sealants often compete with other materials such as polyurethanes, polysulfides, and acrylics. However, the modulus, i.e. elasticity of silicone polymers tends to be in the gigapascal (GPa) range, which does not lend itself to applications that require a lower modulus. Thus, there is a need to develop materials that display the same rubbery properties as silicone polymers but have a modulus that is several orders of magnitude lower than that of silicone polymers.

SUMMARY OF THE INVENTION

An embodiment of the invention is directed to a polymer formed from a mixture of mutually miscible monomers that can be polymerized under ambient conditions and has a tangent delta ranging from 0.1 to 1 at both 20° C. and 37° C.

A further embodiment of the invention is directed to polymers wherein at least one of the mutually miscible monomers is a multifunctional thiol monomer and at least one of the monomers is a multifunctional alkene.

DETAILED DESCRIPTION OF EXEMPLARY EMBODIMENTS

Embodiments of the claimed invention are directed to polymers formed from a mixture of mutually miscible monomers that can be polymerized under ambient conditions and has a tangent delta, as measured by dynamic mechanical analysis at 1 Hz, ranging from 0.1 to 1.0 at both 20° C. and 37° C. In certain embodiments, at least one of the mutually miscible monomers is a multifunctional thiol monomer and at least one other is a multifunctional alkene. In other embodiments, at least one of the mutually miscible monomers is a multifunctional thiol monomer and at least one is a multifunctional alkene, where at least one of the functional C=C (carbon-carbon double bonds) is 1,2-substituted. In further embodiments, at least one of the mutually miscible monomers is a multi-functional thiol monomer and at least one is a multifunctional alkene, where at least two of the functional C=C (carbon-carbon double bonds) are 1,2-substituted.

In some embodiments of the claimed invention, at least one of the mutually miscible monomers is a multifunctional thiol monomer from: Trimethylolpropane tris(3-mercaptopropionate); Trimethylolpropane tris(2-mercaptoacetate); Pentaerythritol tetrakis(2-mercaptoacetate); Pentaerythritol tetrakis(3-mercaptopropionate); 2,2'-(Ethylenedioxy)diethanethiol; 1,3-Propanedithiol; 1,2-Ethanedithiol; 1,4-butanedithiol; Tris[2-(3-mercaptopropionyloxy)ethyl] isocyanurate; 3,4-ethylenedioxythiophene; and at least one other is a multifunctional alkene from: 1,3,5-Triallyl-1,3,5-triazine-2,4,6(1H,3H,5H)-trione; Tricyclo[5.2.1.02,6]decanedimethanol diacrylate; Poly(ethylene glycol) diacrylate; Diallyl terephthalate; Diallyl phthalate; Diallyl maleate; Trimethylolpropane diallyl ether; Ethylene glycol dicyclopentenyl ether acrylate; Diallyl carbonate; diallyl urea; 1,6-Hexanediol diacrylate; Cinnamyl cinnamate; vinyl cinnamate; allyl cinnamate; Allyl acrylate; Crotyl acrylate; Cinnamyl methacrylate; trivinylcyclohexane Polymers of the claimed invention may be formed by a two-step, one-pot reaction process wherein the first step comprises of reducing the functionality of a multifunctional thiol monomer by reaction with a monofunctional alkene. In certain embodiments, the polymer is formed by a two-step, one-pot reaction process wherein the first step comprises of reducing the functionality of a multifunctional alkene monomer by reaction with a monofunctional thiol. Other manufacturing methods include near net shape processing technique such as casting, reaction injection molding, or stereolithography. In some embodiments of the invention, the polymer that is formed in accordance with embodiments of the claimed invention is a thermoset.

Polymers of the claimed invention can be used as substrates for flexible electronic devices such as but not limited to neural interfaces, such as multi-electrode arrays, cochlear implants, nerve cuff electrodes, cortical recording electrodes, peripheral recording electrodes, cortical stimulators and peripheral stimulators. In further embodiments, the polymers can be used as an earplug or as a component in earphones, hearing aids, bluetooth devices or other devices designed to interact with the ear.

In certain embodiments of the invention, the rubbery modulus ranges from 10 kPa to 100 MPa. In certain embodiments, rubbery modulus at 37° C. is between 2-50 times greater than the rubbery modulus at 20° C.

In some embodiments, the polymer comprises monomers wherein all of the monomers have a molecular weight ranging from 750 g/mol to 5000 g/mol. In other embodiments, all of the monomers have a molecular weight below 750 g/mol.

The polymers of the claimed invention optionally comprise antimicrobial additives, photoinitiators, thermal initiators, anaerobic inhibitors, flow agents, stabilizers, fillers or dyes and colorants. In certain embodiments, the polymers comprise a) 0-10 wt % of one or a combination of antimicrobially active silver micro or nanoparticles or glass fillers comprising 45±5 wt. % $SiO_2$, 25±5 wt % $Na_2O$, 25±5 wt % CaO and 5±5 wt % $P_2O_5$ or a combination of antimicrobial additives from the groups of glass fillers or silver micro or nanoparticles; b) 0-10 wt % of one or a combination of photoinitiators whose absorption is in the wavelength near 254 nm UV light or 365 nm UV light, such as 2-2-dimethoxy-2-phenylacetophenone, or in the wavelength range of a laser beam including but not limited to an ND: YV04 laser beam; c) 0-10 wt % or one or a combination of thermal initiators; d) 0-2 wt % of one or a plurality of anaerobic inhibitors in conjunction with those inhibitors acceptable in the processing routes described such as casting, reaction injection molding and stereolithography; e) 0-5 wt % of conventional additives selected from the group consisting of flow agents, and stabilizers; f) 0-90 wt % fillers; and g) 0-5 wt % dyes or colorants, such that the proportion of components a) through g) and the mutually miscible monomers, together equal 100 wt %.

The claimed polymers fulfill a previously unobtainable combination of properties that includes processability, through casting, reaction injection molding or additive manufacturing techniques, significant changes in modulus between 20° C. and 37° C., and high levels of viscoelastic behavior across this temperature range. This set of properties enables devices that can be manufactured into complex shapes, be easily handled at room temperature and subsequently soften to provide a favorable interaction with soft tissues, such as skin, central nervous system tissue and peripheral nervous system tissue. The favorable interaction with skin for example, comes from matching or exceeding the level of viscoelasticity and having a modulus similar to or lower than skin in the use condition.

The claimed polymers have a set of unique properties that make them suitable in manufacturing of near-net shape devices with a viscoelasticity throughout the intended use range, 20° C.-37° C. Specifically the disclosed polymers can be manufactured into near-net shape complex devices by direct polymerization into a mold or by additive techniques such as stereolithography (SLA). This suitability is obtained through the use of mutually miscible monomers that react in a spatially or temporally controlled way, such as with initiation with light and a photoinitiator, to yield ~100% solids in the final part. Additionally the reaction used should be insensitive to mild reaction conditions, such as atmospheric moisture and oxygen. Additionally the monomers are preferably of sufficiently low molecular weight as to allow for low viscosity at 20° C.

The thiol-ene reaction has been described as a "click" reaction for its versatility and facile reaction conditions required to achieve high conversion, even in bulk. Specifically the thiol-ene reaction can proceed through a radical mechanism and result in the stoichiometric addition of thiols to a wide number of alkenes. The resulting polymers of multifunctional thiols and enes have been shown to form highly uniform networks. The thiol-ene reaction is not inhibited by oxygen allowing for simple reaction setups. Low cure stresses are present in the final polymer as there is less volumetric shrinkage and delayed gelation. The presence of the flexible thioether linkage in the final polymer greatly decreases the glass transition temperature ($T_g$) and is therefore suitable for the formation of polymer networks with a $T_g$ near room temperature. Designing polymers with a glass transition near room temperature leads to the desired viscoelasticity and modulus change disclosed herein. In addition to the control over the glass transition that is necessary for the desired viscoelasticity, the modulus at 37° C. is primarily dictated by the crosslink density of the polymer network. The entire range of moduli of interest (1 kPa to 10 MPa) is not readily attainable using previously described combinations of thiol and alkene monomers.

One embodiment uses sequential thiol-ene reactions to first modify either the multi-functional thiol or ene monomer and subsequently polymerize the modified monomer. In FIG. 1 this technique is demonstrated on some exemplary compositions; methyl acrylate is used to selectively react with some of the thiol functional groups of TMICN. The resulting modified monomer is then polymerized with TATATO to rapidly yield a polymer network. By controlling the first monomer modification reaction the modulus and viscoelasticity (value of tan delta) at 20 ° C., modulus and viscoelasticity at 37 ° C. and can be controlled.

Figure 5A:
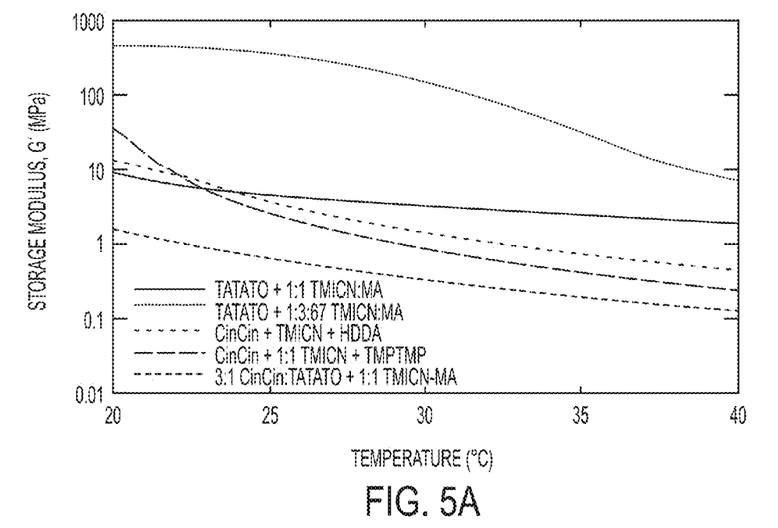
FIG. 5A shows the storage modulus and FIG. 5B shows the tangent delta of exemplary compositions that exhibit desirable properties, in accordance with an embodiment of the invention.
Figure 5B:
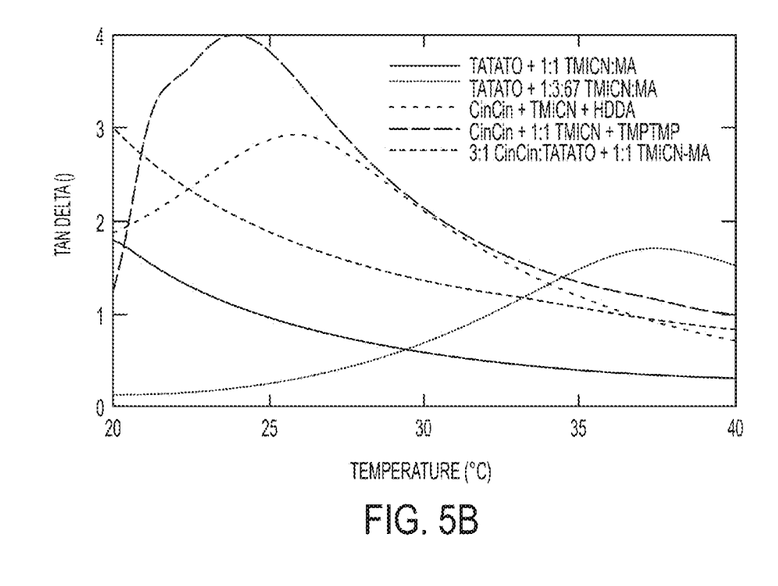

Another embodiment uses alkene monomers with variable reactivity to alter the kinetics of network formation. This subsequently leads to non-ideal networks where the properties cannot be predicted from monomer structure alone. Specifically we use substituted alkenes to control the reactivity towards thiols. Cinnamyl cinnamate (CinCin) a diene where each alkene is phenyl substituted is one example of such a monomer. Exemplary compositions utilizing CinCin to form this types of networks are shown in FIGS. 2-4. FIG. 2 uses the same modified thiol described in the first embodiment and varies a tradition tri-ene monomer (TATATO) with CinCin. Although the glass transition is affected minimally the modulus at 37° C. is reduced more than an order of magnitude. Using unmodified trithiol monomers (TMICN and TMPTMP) allows for roughly equivalent moduli at 37° C., but control over the viscoelasticity at that temperature as shown in FIG. 3. Additionally alkenes such as diacrylates can be added to the reaction mixture. These alkenes homopolymerize in addition to the thiol-ene reaction, leading to higher crosslink density. Monomers that can be used in this process include one or more mutually miscible monomers that are multifunctional thiols including but not limited to:

Trimethylolpropane tris(3-mercaptopropionate); Trimethylolpropane tris(2-mercaptoacetate); Pentaerythritol tetrakis(2-mercaptoacetate); Pentaerythritol tetrakis(3-mercaptopropionate); 2,2'-(Ethylenedioxy)diethanethiol; 1,3-Propanedithiol; 1,2-Ethanedithiol; 1,4-butanedithiol; Tris[2-(3-mercaptopropionyloxy)ethyl] isocyanurate; 3,4-ethylenedioxythiophene and one or more of a combination of multifunctional alkenes including, but not limited to:

1,3,5-Triallyl-1,3,5-triazine-2,4,6(1H,3H,5H)-trione; Tricyclo[5.2.1.02,6]decanedimethanol diacrylate; Poly(ethylene glycol) diacrylate; Diallyl terephthalate; Diallyl phthalate; Diallyl maleate; Trimethylolpropane diallyl ether; Ethylene glycol dicyclopentenyl ether acrylate; Diallyl carbonate; diallyl urea; 1,6-Hexanediol diacrylate; Cinnamyl cinnamate; vinyl cinnamate; allyl cinnamate; Allyl acrylate; Crotyl acrylate; Cinnamyl methacrylate; trivinylcyclohexane FIG. 5 shows a number of exemplary compositions that exhibit properties over the ranges of interest. Shear modulus at 20° C. is controlled to be from 500 MPa to 1.7 MPa. Modulus at 37° C. is shown to be controllable from 16 MPa to 0.17 MPa. The viscoelasticity of the networks (as described by tan delta value measured at 1 Hz) at 20° C. is varied from 0.11 to 3.0. The viscoelasticity of the networks at 37° C. is varied from 0.36 to 1.7. Collectively these compositions cover the range of moduli and viscoelasticity commonly seen in soft tissues, such as skin.

Some notable features of these materials are their ease of processing. Beyond what was described above relating to processing of thiols, the chosen systems are comprised of relatively low molecular weight components, mostly less than 750 g/mol. Other embodiments include components with molecular weights below 1000 g/mol, and yet other below 5000 g/mol. In fact, through reactions like the end-capping reaction described, we can further tune the viscosity of the mutually miscible monomers to meet the needs to different processing or manufacturing environments with only little changes to the bulk thermomechanical properties. For some applications like 3D printing, spin coating, reaction injection molding or casting, the viscosity of the prepolymer is critical to the viability of the processing route to reach desired mechanical properties. Furthermore, the system lends itself to the blending of specific additives such as plasticizers, UV stabilizers, thermal stabilizers, flow agents, antimicrobial particles, dyes, colorants, initiators and fillers. We have described a system that in several embodiments are processed without solvents. This can lead to cost saving and environmentally friendly manufacturing routes and often tighter control of the density and porosity of final parts if there is not the need to extract solvents from the polymer after processing. Furthermore, the avoidance of organic bases like triethylamine and other amine catalysts leads to more adaptability to manufacturing processes that don't want to deal with their removal.

The resulting polymers can be used as substrates for flexible electronic devices such as but not limited to neural interfaces, such as multi-electrode arrays, cochlear implants, nerve cuff electrodes, cortical recording electrodes, peripheral recording electrodes, cortical stimulators and peripheral stimulators. The polymer can also be used as an earplug or as a component in earphones, hearing aids, Bluetooth devices or other devices designed to interact with the ear.

In an embodiment, the polymers can be used to create anatomical models, visualization aids, tissue phantoms, surgical tools or grips thereof, prototypes, or miniatures.

In another embodiment, the polymers can be used to create implantable mechanically robust biomedical devices such as but not limited to suture anchors, stents, rotator cuff anchors, valves, catheters, synthetic ligaments, synthetic tendons, synthetic bones, and synthetic cartilage.

In another embodiment, the polymers can be used to create dental tools and molds. For example in one embodiment, the polymers can be used as dental aligners to help straighten teeth. Polymers can be 3D printed or otherwise manufactured into custom shapes to help guide patients' teeth into predetermined alignments. These materials which can be amorphous and possess extremely high transparency are ideal for this application in which patient acceptance is often tied to limited device visibility. The high optical clarity and other beneficial mechanical properties are a result of the delayed network gelation, controlled network structure and low or zero-cure stress of the thiol-ene reaction in this embodiment that helps maintain mechanical and optical properties during high temperature processing and helps maintain part fidelity to micron resolutions or below.

In another embodiment, the polymers can be used as substrates for composites in which different sized particulate fillers are used to increase the glassy modulus of the materials. In several such embodiments, titanium microparticles, ceramic microparticles, porcelain microparticles or ultrananocrystalline diamond particles could be incorporated into the monomer resin via vortexing, sonication, ultra-sonication, or stirring, or into the polymer by means of chaotic mixing such as planetary mixing or other forms of highly dispersive or high shear force mixing. The resulting composites can be used in a host of mentioned applications. One such specific application is the design of a root canal tool in which a polymer composite can be used to help a dentist remove fascia from the root canal via a drill bit that is less stiff than conventional metal drill bits. In a more specific embodiment, the root canal drill bit can be made from a shape memory polymer composite which can be dynamically reshaped.

In another embodiment, the polymers can be used to create components of custom prosthetics or plastic surgical implants including but not limited to limbs, hands, feet, fingers, toes, breasts, genitalia, ears, lips, and noses. In this embodiment, the devices could possess shape memory abilities, such that users can train and retrain these parts into metastable shapes. For example, polymer with an onset of glass transition temperature above body temperature and normal use temperatures (such as but not limited to glass transition temperatures of 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C. or 80° C.). These materials for instance could be heated and molded with heat sources such as hair dryers, heat guns, hot water, heat packs, sodium acetate, resistive heaters or others. In other embodiments, the glass transition temperature could be below body temperature such that soft or viscoelastic properties are desired during normal use.

In yet another embodiment, the polymers can be used to create bobble-head dolls, adult novelties, action figures, cell phone casings, tool grips, children's toys, or athletic equipment.

In a further embodiment, the polymers can be used in high temperature applications. For instance combinations of these materials can be used in environments up to about 100° C., above about 100° C., above about 150° C., above about 200° C., above about 250° C. and above about 270° C. In addition, materials in one embodiment can be used at temperatures above about 270° C., in which the environment leads to a controlled degradation.

In another embodiment, the polymers can be used in applications in the oil and gas industry including but not limited to down hole applications, well cementing applications, steam cracking applications, fracking applications, merox treatment, distillation applications, or as cementing additives, gaskets, fixtures, housings, drill coverings, dielectrics, encapsulants, hinges, struts, and structural supports. In particular these materials may find particular use because of resistance to extreme environments, chemicals and pressures. This is a result of the delayed network gelation, controlled network structure and low or zero-cure stress of the thiol-ene reaction in specific embodiments that help maintain mechanical properties well above the polymers' glass transition temperatures. This makes these materials extremely useful for high temperature applications. Furthermore, the ability to mass manufacture or rapidly custom manufacture these materials through bulk or additive manufacturing could lead to low initial costs and low maintenance costs.

Relevant processing: The polymers described herein can be manufactured via conventional thermoplastic or thermoset processing or as a result of additive manufacturing such as fused filament fabrication (FFF), selective laser sintering (SLS), SLA, or additive manufacturing systems that utilize Digital Light Projection Technology to selectively cure resins into the described polymers.

Relevant Chemical Structures: Certain of these structures are referred to by acronym in the accompanying figures Tris[2-(3-mercaptopropionyloxy)ethyl] isocyanurate (TMICN)

Trimethylolpropane tris(3-mercaptopropionate) (TMPTMP)

Pentaerythritol tetrakis(3-mercaptopropionate) (PETMP)

1,3,5-Triallyl-1,3,5-triazine-2,4,6(1H,3H,5H)-trione (TATATO)

MethylAcrylate (MA)

Poly (ethylene glycol) diacrylate (PEGDA)

Hexane Diol Diacrylate (HDDA)

Cinnamyl Cinnamate (CinCin)

Allyl cinnamate (AllCin)

Vinyl cinnamate (VinCin)

Figure 1A:
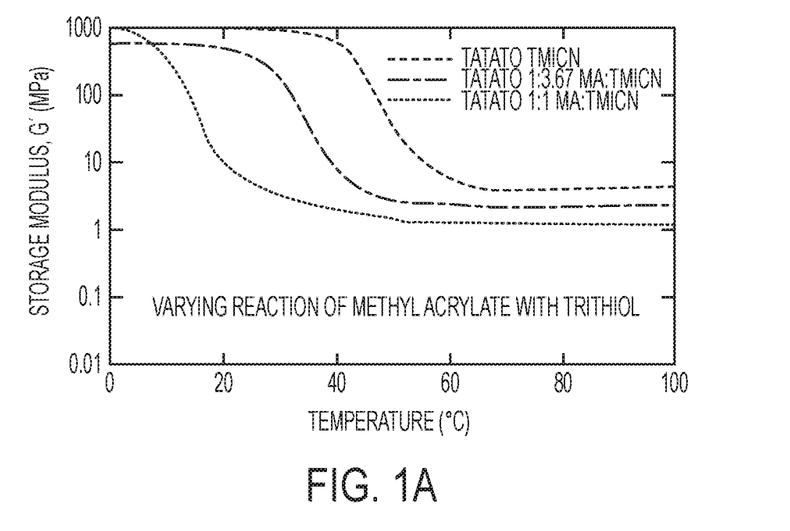
FIG. 1A shows the storage modulus and FIG. 1B shows the tangent delta of multi-functional thiol monomers, in accordance with an embodiment of the invention.
Figure 1B:
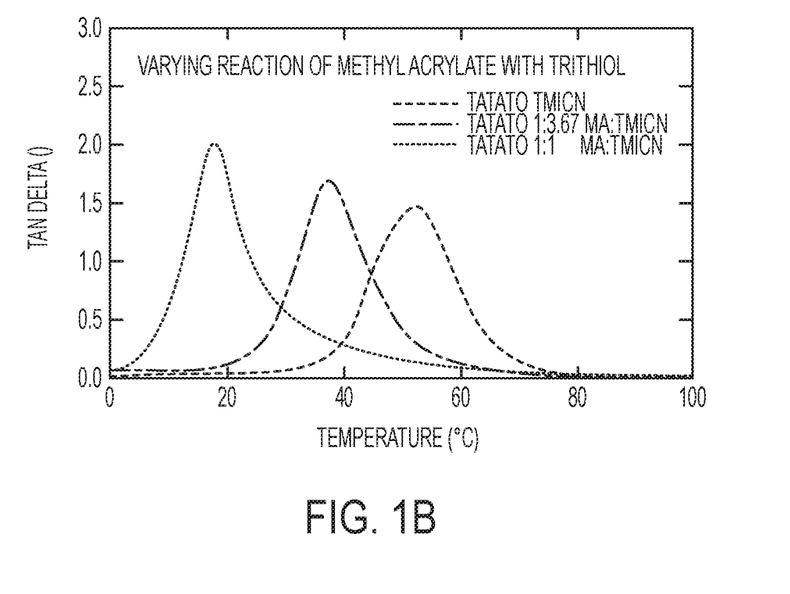

FIG. 1 shows a method for end-capping pendant thiol groups on multi-functional thiol monomers in order to reduce the crosslink density in the resulting polymer networks. In this embodiment, MA is reacted with TMICN in a functional stoichiometric 1:1 ratio such that on average one of the three pendant thiol end groups is capped. This new monomer is then reacted in varying ratios with -ene monomers such as TATATO. This technique enables precise control of glass transition temperature and of the rubbery modulus shown through dynamic mechanical analysis: temperature ramps drive changes in storage modulus (FIG. 1A) and tangent delta (FIG. 1B). The reactions are facile one-pot synthesis techniques that first involve monomer modifications and second involve polymerizations. This allows the creation of a wide range of stable two part systems that can be later reacted to form polymer networks with specific properties.

Figure 2A:
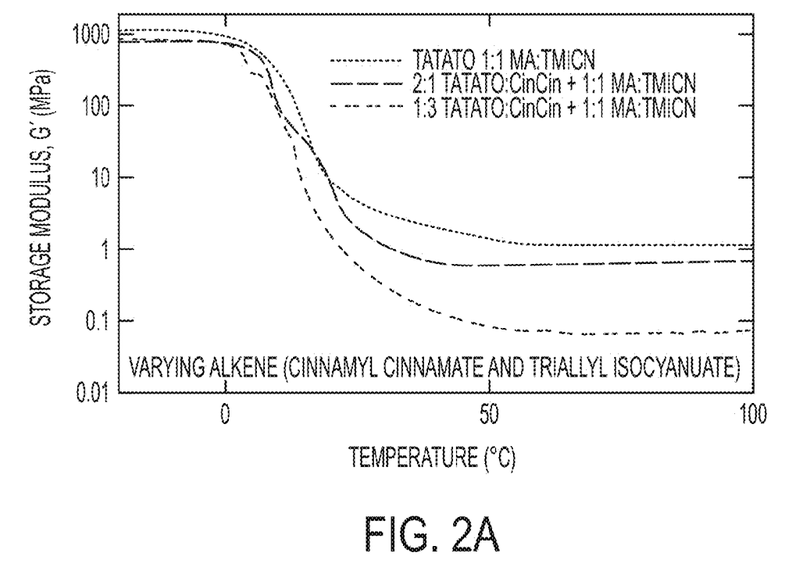
FIG. 2A shows the storage modulus and FIG. 2B shows the tangent delta of multi-functional thiol monomers upon addition of cinnamyl cinnamate, in accordance with an embodiment of the invention.
Figure 2B:
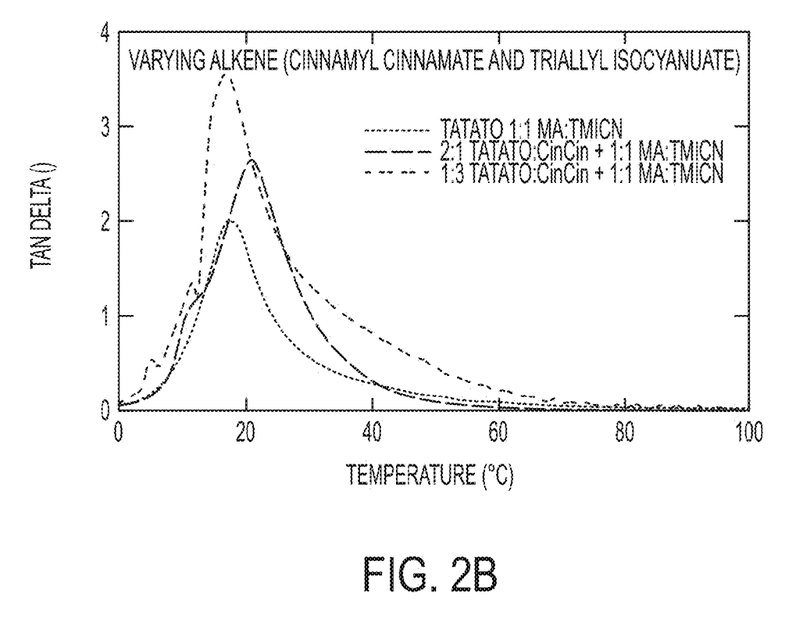

FIG. 2 demonstrates polymer systems using the thiol end capping approach described in FIG. 1 and reaction with different -ene monomers. We show a repeat curve from FIG. 1 of TATAO+1:1 MA:TMICN for reference and demonstrate the addition of addition of varying ratios of Cinnamyl Cinnamate (a natural food additive) (CinCin). FIG. 2A shows the unique network structure that forms allows modification of the rubbery modulus from above 1 MPa in shear down to 100 kPa in shear with very minimal changes to the glass transition of the polymer. This strategy is very important for the modification of softening polymers in the room temperature and body temperature environments. FIG. 2B shows the tangent delta or the ratio of the loss modulus to the storage modulus is pictured. Several compositions exhibit unusually high tangent delta values indicating excellent damping properties.

Figure 3A:
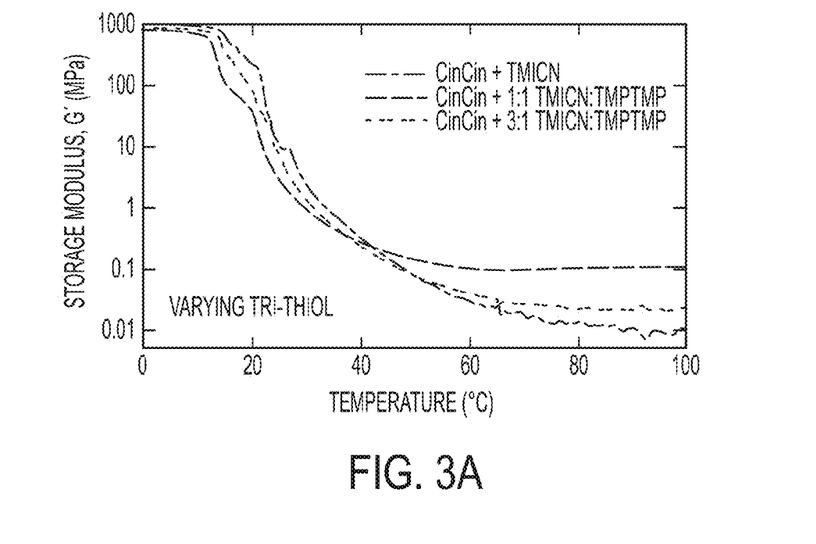
FIG. 3A shows the storage modulus and FIG. 3B shows the tangent delta of multi-functional thiol monomers upon addition of cinnamyl cinnamate and varying the ratio of the thiol monomers, in accordance with an embodiment of the invention.
Figure 3B:
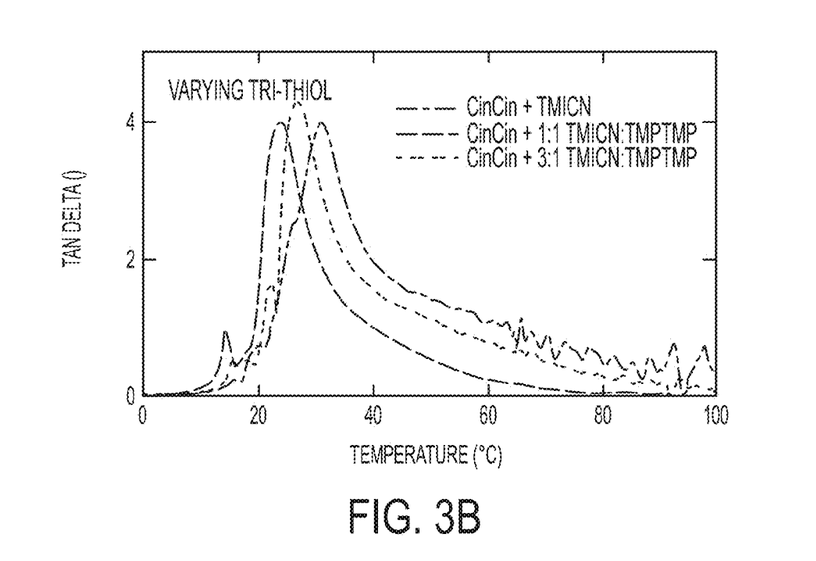
Figure 4:
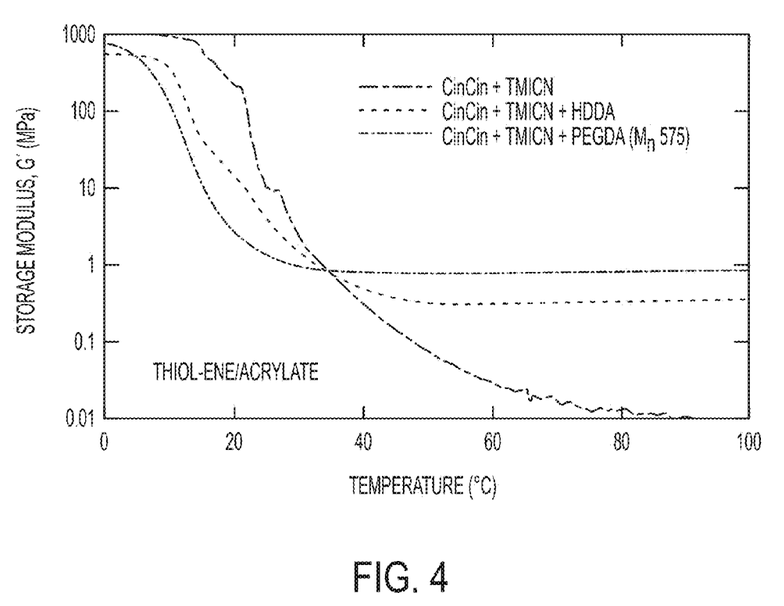
FIG. 4 shows the storage modulus of mixed mode thiol-ene/acrylate networks in accordance with an embodiment of the invention.

FIG. 3A shows polymer systems that have been developed that soften from 1 GPa in shear to below 10 kPa in shear through the glass transition temperature using CinCin as the -ene monomer. Tunability has been demonstrated in this system in addition to what has been shown previously by altering the ratio of chosen thiol monomers. In this embodiment, by varying the concentration of select thiol monomers (TMICN and TMPTMP) in stoichiometric functional molar ratios with CinCin we can tune the thermomechanical properties (e.g. rubbery modulus) of the resulting polymer network. In FIG. 3B, even higher tangent delta values emerge than in FIG. 2 when using CinCin monomers with a variety of tri-thiols.

FIG. 4 shows mixed mode thiol-ene/acrylate networks can also be used to build softening polymer systems that are compatible with various processing schemes.

FIG. 5 describes several of the embodiments of the softening materials between 20° C. and 37° C. Materials in these embodiments have a 5 to 100 fold modulus decrease within this temperature range. Each of these compositions exhibits significant viscoelasticity over the entire temperature range.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are with the scope of this disclosure.

What is claimed is:

1. A polymer formed from a mixture of mutually miscible monomers that can be polymerized under ambient conditions, wherein:
   one of the mutually miscible monomers includes a multifunctional thiol monomer including Tris[2-(3-mercaptopropionyloxy)ethyl]isocyanurate; and
   another one of the mutually miscible monomer includes one or more multifunctional alkenes of Tricyclo[5.2.1.02,6]decanedimethanol diacrylate and another multifunctional alkene selected from the group consisting of:
   Poly(ethylene glycol) diacrylate; Diallyl terephthalate; Diallyl phthalate; Diallyl maleate; Trimethylolpropane diallyl ether; Ethylene glycol dicyclopentenyl ether acrylate; Diallyl carbonate; diallyl urea; 1,6- Hexanediol diacrylate; Cinnamyl cinnamate; vinyl cinnamate; allyl cinnamate; Allyl acrylate; Crotyl acrylate; Cinnamyl methacrylate; and trivinylcyclohexane.

2. The polymer of claim 1, wherein the polymer has a tangent delta greater than 0.1 at both 20° C. and 37° C., as measured by dynamic mechanical analysis at 1Hz.

3. The polymer of claim 1, wherein the polymer has a tangent delta greater than 0.1 at both 40° C. and 57° C., as measured by dynamic mechanical analysis at 1Hz.

4. The polymer of claim 1, wherein the polymer has a tangent delta greater than 0.1 at both 55° C. and 72° C., as measured by dynamic mechanical analysis at 1Hz.

5. The polymer of claim 1, wherein the polymer has a rubbery modulus at 47° C. that is between 2-50 times less than the glassy modulus of the polymer at 30° C.

6. The polymer of claim 1, wherein the polymer has a rubbery modulus at 57° C. that is between 2-50 times less than the glassy modulus of the polymer at 40° C.

7. The polymer of claim 1, wherein the polymer has a tangent delta in the range from 0.1 to 1.

8. The polymer of claim 1, wherein one of the functional C=C (carbon-carbon double bonds) is 1,2-substituted in the multifunctional alkene.

9. The polymer of claim 1, wherein two of the functional C=C (carbon-carbon double bonds) are 1,2-substituted in the multifunctional alkene.

10. The polymer of claim 1, wherein the polymer has a rubbery modulus in a range from 10 kPa to 100 MPa.

11. A composite comprising:
    the polymer of claim 1,
    at least one particulate filler; and
    at least one carbon based filler, wherein the glassy modulus of the composite is above 1 GPa.

12. The composite of claim 11, wherein the glassy modulus of the composite is above 5 GPa.

13. The composite of claim 11, wherein the at least one particulate filler is selected from ceramic, metallic and polymeric fillers.

14. The composite of claim 11, wherein the at least one carbon based filler is nanocrystalline diamond.

15. The polymer of claim 1, wherein the polymer has a rubbery modulus at 37° C. that is between 2-50 times less than the glassy modulus of the polymer at 20° C.

16. The polymer of claim 1 wherein all of the monomers have a molecular weight below 5000 g/mol.

17. The polymer of claim 1 wherein all of the monomers have a molecular weight below 750 g/mol.

18. A polymer formed from a mixture of mutually miscible monomers that can be polymerized under ambient conditions, wherein:
    at least one of the mutually miscible monomers is a multifunctional thiol monomer modified such that some pendant thiol end groups of the multifunctional thiol monomer are end-capped by reaction with a monofunctional alkene monomer, and at least one of the monomers is a multifunctional alkene monomer;
    the multifunctional thiol monomer includes Tris[2-(3-mercaptopropionyloxy)ethyl]isocyanurate; and
    the multifunctional alkene includes 1,3,5-Triallyl-1,3,5-triazine-2,4,6(1H,3H,5H)-trione and Tricyclo[5.2.1.02,6]decanedimethanol diacrylate.

19. A polymer formed from a mixture of mutually miscible monomers that can be polymerized under ambient conditions, wherein:
    one of the mutually miscible monomers includes a multifunctional thiol monomer selected from the group consisting of:
    Trimethylolpropane tris(2-mercaptoacetate); 2.2'-(Ethylenedioxy)diethanethiol; 1,2-Ethanedithiol; 1,4-butanedithiol; Tris[2-(3-mercaptopropionyloxy)ethyl]isocyanurate; and 3,4-ethylenedioxythiophene; and
    another one of the mutually miscible monomer includes a multifunctional alkene monomer selected from the group consisting of:
    Diallyl terephthalate; Diallyl phthalate; Ethylene glycol dicyclopentenyl ether acrylate; Diallyl carbonate; diallyl urea; Cinnamyl cinnamate; vinyl cinnamate; allyl cinnamate; Allyl acrylate; Crotyl acrylate; and Cinnamyl methacrylate.

20. A polymer formed from a mixture of mutually miscible monomers that can be polymerized under ambient conditions, wherein:

at least one of the mutually miscible monomers is a multifunctional thiol monomer having three or four pendant thiol end groups modified such that on average from about 0.07 to 0.1 of the pendant thiol end groups are end-capped by reaction with a monofunctional alkene monomer, and at least one of the monomers is a multifunctional alkene monomer, wherein a ratio of the monofunctional alkene monomer reacted with the multifunctional thiol monomer equals 1:3.67.

21. The polymer of claim 20, wherein the multifunctional thiol monomer is selected from the group consisting of:
Trimethylolpropane tris(3-mercaptopropionate); Trimethylolpropane tris(2-mercaptoacetate); Pentaerythritol tetrakis(2-mercaptoacetate); Pentaerythritol tetrakis(3-mercaptopropionate); Tris[2-(3-mercaptopropionyloxy)ethyl]isocyanurate; and
the multifunctional alkene monomer is selected from the group consisting of:
1,3,5-Triallyl-1,3,5-triazine-2,4,6(1H,3H,5H)-trione; Tricyclo[5.2.1.02,6]decanedimethanol diacrylate; Poly(ethylene glycol) diacrylate; Diallyl terephthalate; Diallyl phthalate; Diallyl maleate; Trimethylolpropane diallyl ether; Ethylene glycol dicyclopentenyl ether acrylate; Diallyl carbonate; diallyl urea; 1,6- Hexanediol diacrylate; Cinnamyl cinnamate; vinyl cinnamate; allyl cinnamate; Allyl acrylate; Crotyl acrylate; Cinnamyl methacrylate; and trivinylcyclohexane.

22. The polymer of claim 20, wherein the monofunctional alkene monomer is methyl acrylate.

* * * * *

UNITED STATES PATENT AND TRADEMARK OFFICE
CERTIFICATE OF CORRECTION

PATENT NO. : 9,931,771 B2  
APPLICATION NO. : 14/261336  
DATED : April 3, 2018  
INVENTOR(S) : Walter Voit et al.

Page 1 of 1

It is certified that error appears in the above-identified patent and that said Letters Patent is hereby corrected as shown below:

In the Specification

In Column 7, Line 66, after  delete "1,3,5-Trially-1,3,5-triazine-2,4,6(1H,3H,5H)-trione (TATATO)1" and please insert --1,3,5-Triallyl-1,3,5-triazine-2,4,6(1H,3H,5H)-trione (TATATO)1--

Signed and Sealed this  
Twenty-eighth Day of August, 2018

Andrei Iancu  
*Director of the United States Patent and Trademark Office*